(12) United States Patent
Lebel et al.

(10) Patent No.: US 8,105,268 B2
(45) Date of Patent: Jan. 31, 2012

(54) SAFETY LIMITS FOR CLOSED-LOOP INFUSION PUMP CONTROL

(75) Inventors: Ronald J. Lebel, Sherman Oaks, CA (US); Timothy Starkweather, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 12/907,454

(22) Filed: Oct. 19, 2010

(65) Prior Publication Data
US 2011/0034909 A1 Feb. 10, 2011

Related U.S. Application Data

(62) Division of application No. 12/490,006, filed on Jun. 23, 2009, now Pat. No. 7,850,641, which is a division of application No. 10/979,980, filed on Nov. 3, 2004, now Pat. No. 7,569,030, which is a division of application No. 10/033,530, filed on Dec. 26, 2001, now Pat. No. 6,827,702.

(60) Provisional application No. 60/318,062, filed on Sep. 7, 2001, provisional application No. 60/335,664, filed on Oct. 23, 2001.

(51) Int. Cl.
*A61M 31/00* (2006.01)

(52) U.S. Cl. ........................................................ 604/66

(58) Field of Classification Search .............. 604/65–67, 604/131; 128/DIG. 12, DIG. 13
See application file for complete search history.

(56) References Cited

U.S. PATENT DOCUMENTS

| | | | |
|---|---|---|---|
| 3,621,357 A | 11/1971 | Kubo et al. | |
| 3,826,887 A | 7/1974 | Pemberton | |
| 3,834,617 A | 9/1974 | Dyntar | |
| 3,986,571 A | 10/1976 | Strobel et al. | |
| 4,055,175 A * | 10/1977 | Clemens et al. | 604/66 |
| 4,077,405 A | 3/1978 | Haerten et al. | |
| 4,080,966 A | 3/1978 | McNally et al. | |
| 4,151,845 A | 5/1979 | Clemens | |
| 4,245,634 A | 1/1981 | Albisser et al. | |
| 4,280,494 A | 7/1981 | Cosgrove et al. | |
| 4,282,872 A | 8/1981 | Franetzki et al. | |
| 4,291,692 A | 9/1981 | Bowman et al. | |

(Continued)

FOREIGN PATENT DOCUMENTS
DE 100 06 044 A1 8/2001

(Continued)

OTHER PUBLICATIONS

"Once Daily Glucotrol XL (glipiside) extended release", May 1996; 45(suppl 2): 123A, Abstract 450.

(Continued)

*Primary Examiner* — Manuel Mendez
(74) *Attorney, Agent, or Firm* — Foley & Lardner LLP

(57) ABSTRACT

A system and process for providing safety limits on the delivery of an infusion formulation by an infusion pump system in response to a sensed biological state. The safety limits may comprise user-initiated event signals corresponding to events that may significantly affect the biological state. The safety limits may further comprise user-initiated event ranking signals for respective events which specify a degree, quantity, or measure for the respective event. The user-initiated event and event ranking signals may be communicated to a computing element associated with the infusion pump by an associated communication device having a user interface which comprises a plurality of user-selectable operators for entering information about the events and event rankings.

34 Claims, 9 Drawing Sheets

U.S. PATENT DOCUMENTS

| | | | |
|---|---|---|---|
| 4,433,072 A | 2/1984 | Pusineri et al. |
| 4,475,901 A | 10/1984 | Kraegen et al. |
| 4,494,950 A | 1/1985 | Fischell |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,726 A | 3/1988 | Allen, III |
| 4,781,798 A | 11/1988 | Gough |
| 4,786,394 A | 11/1988 | Enzer et al. |
| 4,871,351 A | 10/1989 | Feingold |
| 5,050,612 A | 9/1991 | Matsumura |
| 5,068,536 A | 11/1991 | Rosenthal |
| 5,080,653 A | 1/1992 | Voss et al. |
| 5,097,122 A | 3/1992 | Colman et al. |
| 5,101,814 A | 4/1992 | Palti |
| 5,108,819 A | 4/1992 | Heller et al. |
| 5,139,020 A | 8/1992 | Koestner et al. |
| 5,165,407 A | 11/1992 | Wilson et al. |
| 5,190,041 A | 3/1993 | Palti |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,356,786 A | 10/1994 | Heller et al. |
| 5,370,622 A | 12/1994 | Livingston et al. |
| 5,371,687 A | 12/1994 | Holmes et al. |
| 5,376,070 A | 12/1994 | Purvis et al. |
| 5,390,671 A | 2/1995 | Lord et al. |
| 5,391,250 A | 2/1995 | Cheney et al. |
| 5,403,700 A | 4/1995 | Heller et al. |
| 5,411,647 A | 5/1995 | Johnson et al. |
| 5,474,552 A | 12/1995 | Palti |
| 5,482,473 A | 1/1996 | Lord et al. |
| 5,497,772 A | 3/1996 | Schulman et al. |
| 5,507,288 A | 4/1996 | Bocker et al. |
| 5,536,249 A | 7/1996 | Castellano et al. |
| 5,543,326 A | 8/1996 | Heller et al. |
| 5,558,640 A | 9/1996 | Pfeiler et al. |
| 5,569,186 A * | 10/1996 | Lord et al. ............. 604/67 |
| 5,586,553 A | 12/1996 | Halili et al. |
| 5,593,390 A | 1/1997 | Castellano et al. |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,695,464 A | 12/1997 | Viallet |
| 5,713,856 A | 2/1998 | Eggers et al. |
| 5,728,074 A | 3/1998 | Castellano et al. |
| 5,730,137 A | 3/1998 | Amano et al. |
| 5,745,362 A | 4/1998 | Hiroi et al. |
| 5,750,926 A | 5/1998 | Schulman et al. |
| 5,771,890 A | 6/1998 | Tamada |
| 5,779,665 A | 7/1998 | Mastrototaro et al. |
| 5,791,344 A | 8/1998 | Schulman et al. |
| 5,813,403 A | 9/1998 | Soller et al. |
| 5,822,715 A | 10/1998 | Worthington et al. |
| 5,830,133 A | 11/1998 | Osten et al. |
| 5,860,919 A | 1/1999 | Kiani-Azarbayjany et al. |
| 5,885,211 A | 3/1999 | Eppstein et al. |
| 5,904,708 A | 5/1999 | Goedeke |
| 5,917,346 A | 6/1999 | Gord |
| 5,925,021 A | 7/1999 | Castellano et al. |
| 5,956,501 A | 9/1999 | Brown |
| 5,965,380 A | 10/1999 | Heller et al. |
| 5,972,199 A | 10/1999 | Heller et al. |
| 5,995,860 A | 11/1999 | Sun et al. |
| 5,999,848 A | 12/1999 | Gord et al. |
| 5,999,849 A | 12/1999 | Gord et al. |
| 6,001,065 A | 12/1999 | Devito |
| 6,043,437 A | 3/2000 | Schulman et al. |
| 6,049,727 A | 4/2000 | Crothall |
| 6,064,896 A | 5/2000 | Rosenthal |
| 6,081,736 A | 6/2000 | Colvin et al. |
| 6,083,710 A | 7/2000 | Heller et al. |
| 6,088,608 A | 7/2000 | Schulman et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,180,416 B1 | 1/2001 | Kurnik et al. |
| 6,221,009 B1 | 4/2001 | Doi et al. |
| 6,233,471 B1 | 5/2001 | Berner et al. |
| 6,233,539 B1 | 5/2001 | Brown |
| 6,259,937 B1 | 7/2001 | Schulman et al. |
| 6,272,364 B1 | 8/2001 | Kurnik |
| 6,326,160 B1 | 12/2001 | Dunn et al. |
| 6,329,161 B1 | 12/2001 | Heller et al. |
| 6,354,299 B1 | 3/2002 | Fischell et al. |
| 6,379,301 B1 | 4/2002 | Worthington et al. |
| 6,416,293 B1 | 7/2002 | Bouchard et al. |
| 6,424,873 B1 | 7/2002 | Przybylski |
| 6,453,195 B1 | 9/2002 | Thompson |
| 6,472,122 B1 | 10/2002 | Schulman et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,212 B2 | 4/2003 | Galley et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,749,740 B2 | 6/2004 | Liamos et al. |
| 6,804,558 B2 | 10/2004 | Haller et al. |
| 6,809,653 B1 | 10/2004 | Mann et al. |
| 6,881,551 B2 | 4/2005 | Heller et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,931,328 B2 | 8/2005 | Braig et al. |
| 6,932,894 B2 | 8/2005 | Mao et al. |
| 6,942,518 B2 | 9/2005 | Liamos et al. |
| 6,973,706 B2 | 12/2005 | Say et al. |
| 6,975,893 B2 | 12/2005 | Say et al. |
| 7,003,340 B2 | 2/2006 | Say et al. |
| 7,018,735 B2 | 3/2006 | Heller |
| 7,025,760 B2 | 4/2006 | Miller et al. |
| 7,041,468 B2 | 5/2006 | Drucker et al. |
| 7,052,591 B2 | 5/2006 | Gao et al. |
| 7,058,437 B2 | 6/2006 | Buse et al. |
| 7,138,330 B2 | 11/2006 | Shah et al. |
| 7,162,289 B2 | 1/2007 | Shah et al. |
| 7,167,818 B2 | 1/2007 | Brown |
| 7,201,977 B2 | 4/2007 | Li et al. |
| 7,247,138 B2 | 7/2007 | Reghabi et al. |
| 7,267,665 B2 | 9/2007 | Steil et al. |
| 2003/0028089 A1 | 2/2003 | Galley et al. |
| 2004/0061232 A1 | 4/2004 | Shah et al. |

| | | | |
|---|---|---|---|
| 2004/0064133 | A1 | 4/2004 | Miller et al. |
| 2004/0074785 | A1 | 4/2004 | Holker et al. |
| 2005/0272640 | A1 | 12/2005 | Doyle et al. |

FOREIGN PATENT DOCUMENTS

| | | |
|---|---|---|
| EP | 1 338 295 A1 | 8/2003 |
| JP | 01-317452 | 12/1989 |
| JP | 07-132142 | 5/1995 |
| JP | 07-148253 | 6/1995 |
| JP | 09-504974 | 5/1997 |
| JP | 10 504729 | 5/1998 |
| WO | WO-95/13838 | 5/1995 |
| WO | WO-96/37246 A1 | 11/1996 |
| WO | WO-98/02086 | 1/1998 |
| WO | WO-99/29230 A1 | 6/1999 |
| WO | WO-99/58050 A1 | 11/1999 |
| WO | WO-00/10628 A2 | 3/2000 |
| WO | WO-00/49941 A1 | 8/2000 |
| WO | WO-00/74753 A1 | 12/2000 |
| WO | WO-02/058537 A2 | 8/2002 |
| WO | WO-03/006091 A1 | 1/2003 |
| WO | WO-03/080157 A1 | 10/2003 |
| WO | WO-2004/060455 A1 | 7/2004 |

OTHER PUBLICATIONS

Abel et al., (1984) "Experience with an Implantable Glucose Sensor as a Prerequisite of an Aritificial Beta Cell," Biomed. Biochim. Acta 43, 5, pp. 577-584.

Bellazi et al., "The Subcutaneous Route to Insulin-Dependent Diabetes Therapy," IEEE Engineering in Medicine and Biology, Jan./Feb. 2001, pp. 54-64.

Bindra et al., "Design and In Vitro Studies of a Needle-Type Glucose Sensor for Subcutaneous Monitoring," Anal. Chem., Sep. 1991, vol. 63, No. 17, pp. 1692-1696.

Boguslavsky et al., "Applications of Redox Polymers in Biosensors," Solid State Ionics, 1993, vol. 60, pp. 189-197.

Office Action dated Dec. 20, 2010 from related Canadian Patent Application No. 2,459,398.

Office Action dated Jul. 20, 2010 from related U.S. Appl. No. 10/850,637.

Office Action dated Nov. 15, 2010 from related European Patent Application No. 02 766 221.2-2401.

Office Action dated Sep. 9, 2008 issued from related Japanese Patent Application No. 2003-526454.

PCT Search Report for International Application No. PCT/US00/15393, Pub. date: Dec. 14, 2000.

PCT Search Report for International Application No. PCT/US03/13199, Pub. date: Nov. 20, 2003.

PCT Search Report for International Application No. PCT/US03/41650, Pub. date: Jul. 22, 2004.

PCT Search Report for International Application No. PCT/US2006/003350, Pub. date: Aug. 10, 2006.

US Notice of Allowance dated Nov. 5, 2010 from related U.S. Appl. No. 10/850,637.

US Notice of Allowance on dated Sep. 22, 2010 from related U.S. Appl. No. 12/490,006.

US Office Action dated Jun. 21, 2010 from related U.S. Appl. No. 12/490,006.

Csoregi et al., "Design, Characterization, and One-Point in Vivo Calibration of a Subcutaneously Implanted Glucose Electrode," Anal. Chem., Oct. 1994, vol. 66, No. 19, pp. 3131-3138.

Decision of Rejection received for JP 2003-526454 dated Mar. 31, 2009.

Doran et al., "Derivative Weighted Active Insulin Control Modelling and Clinical Trials for ICU Patients," Medical Engineering & Physics, 2004, vol. 26, pp. 855-866.

Geise et al., "Electropolymerized 1,3-diaminobenzene for the Construction of a 1,1'-dimethylferrocene Mediated Glucose Biosensor," Analytica Chimica Acta, 1993, vol. 281, pp. 467-473.

Gernet et al., "A Planar Glucose Enzyme Electrode," Sensors and Actuators, 1989, vol. 17, pp. 537-540.

Gernet et al., "Fabrication and Characterization of a Planar Electrochemical Cell and Its Application as a Glucose Sensor," Sensors and Actuators, 1989, vol. 18, pp. 59-70.

Gorton et al., "Amperometric Biosensors Based on an Apparent Direct Electron Transfer Between Electrodes and Immobilized Peroxidases," Analyst, Aug. 1992, vol. 117, pp. 1235-1241.

Gorton et al., "Amperometric Glucose Sensors Based on Immobilized Glucose-Oxidizing Enzymes and Chemically Modified Electrodes," Analytica Chimica Acta, 1991, vol. 249, pp. 43-54.

Gough et al., "Two-Dimensional Enzyme Electrode Sensor for Glucose," Analytical Chemistry, 1985, vol. 57, pp. 2351-2357.

Gregg et al., "Cross-Linked Redox Gels Containing Glucose Oxidase for Amperometric Biosensor Applications," Anal. Chem., 1990, vol. 62, pp. 258-263.

Gregg et al., "Redox Polymer Films Containing Enzymes," J. Phys. Chem., 1991, vol. 95, pp. 5970-5975.

Hashiguchi et al., "Development of a Miniaturized Glucose Monitoring System by Combining a Needle-Type Glucose Sensor With Microdialysis Sampling Method," Diabetes Care, May 1994, vol. 17, No. 5, pp. 387-389.

Heller, "Electrical Wiring of Redox Enzymes," Accounts of Chemical Research, May 1990, vol. 23, No. 5, pp. 128-134.

International Search Report received for PCT/US2002/028022 dated Apr. 23, 2003.

International Search Report received for PCT/US2002/28015 dated Jul. 30, 2003.

Jobst et al., "Thin-Film Microbiosensors for Glucose-Lactate Monitoring," Analytical Chemistry, Sep. 1996, vol. 68, No. 18, pp. 3173-3179.

Johnson et al., "In vivo Evaluation of an Electroenzymatic Glucose Sensor Implanted in Subcutaneous Tissue," Biosensors & Bioelectronics, 1992, vol. 7, pp. 709-714.

Jonsson et al., "An Electrochemical Sensor for Hydrogen Peroxide Based on Peroxidase Adsorbed on a Spectrographic Graphite Electrode," Electroanalysis, 1989, vol. 1, No. 5, pp. 465-468.

Kanapieniene et al., "Miniature Glucose Biosensor with Extended Linearity," Sensors and Actuators, 1992, vol. B, No. 10, pp. 37-40.

Kawamori et al., "Perfect Normalization of Excessive Glucagon Responses to Intravenous Arginine in Human Diabetes Mellitus with the Artficial Beta-Cell," Diabetes, Sep. 1980, vol. 29, pp. 762-765.

Kimura et al., "An Immobilized Enzyme Membrane Fabrication Method Using an Ink Jet Nozzle," Biosensors, 1988, vol. 4, pp. 41-52.

Koudelka et al., "In-vivo Behaviour of Hypodermically Implanted Microfabricated Glucose Sensors," Biosensors & Bioelectronics, 1991, vol. 6, pp. 31-36.

Koudelka et al., "Planar Amperometric Enzyme-Based Glucose Microelectrode," Sensors and Actuators, 1989, vol. 18, pp. 157-165.

Mastrototaro et al., "An Electroenzymatic Glucose Sensor Fabricated on a Flexible Substrate," Sensors and Actuators, vol. B, No. 5, pp. 139-144, (1991).

Mastrototaro et al., "An Electroenzymatic Sensor Capable of 72 Hour Continuous Monitoring of Subcutaneous Glucose," 14th International Diabetes Federation Congress, Jun. 1991, 19 pages.

McKean et al., "A Telemetry-Instrumentation System for Chronically Implanted Glucose and Oxygen Sensor," IEEE Transactions on Biomedical Engineering, Jul. 1988, vol. 35, No. 7, pp. 526-532.

Monroe, "Novel Implantable Glucose Sensors," ACL, Dec. 1989, pp. 8-16.

Morff et al., "Microfabrication of Reproducible, Economical, Electroenzymatic Glucose Sensors," Annual International Conference of the IEEE Engineering in Medicine and Biology Society, 1990, vol. 12, No. 12, pp. 483-484.

Moussy et al., "Performance of Subcutaneously Implanted Needle-Type Glucose Sensors Employing a Novel Trilayer Coating," Anal. Chem., 1993, vol. 65, pp. 2072-2077.

Nakamoto et al., "A Lift-Off Method for Patterning Enzyme-Immobilized Membranes in Multi-Biosensors," Sensors and Actuators, 1988, vol. 13, pp. 165-172.

Nishida et al., "Clinical Applications of the Wearable Artificial Endocrine Pancreas with the Newly Designed Needle-Type Glucose Sensors," Pathogenesis and Treatment of NIDDM, 1994, pp. 353-358.

Nishida et al., "Development of a Ferrocene-Mediated Needle-Type Glucose Sensor Covered with Newly Designed Biocompatible Membrane, 2-methacryloyloxyethyl phosphorylcholine-co-n-butylmethacrylate," Medical Progress Through Technology, 1995, vol. 21, pp. 91-103.

Non-final Office Action received for U.S. Appl. No. 10/033,173 dated Jul. 10, 2003.
Non-final Office Action received for U.S. Appl. No. 10/033,530 dated May 6, 2004.
Non-final Office Action received for U.S. Appl. No. 10/850,637 dated Aug. 19, 2008.
Non-final Office Action received for U.S. Appl. No. 10/850,637 dated Dec. 30, 2009.
Non-final Office Action received for U.S. Appl. No. 10/979,980 dated Dec. 17, 2008.
Notice of Allowance received for U.S. Appl. No. 10/033,530 dated Sep. 21, 2004.
Notice of Allowance received for U.S. Appl. No. 10/979,980 dated Apr. 30, 2009.
Notice of Allowance received on U.S. Appl. No. 10/033,173 dated Jan. 27, 2004.
Office Action received for CA 2,459,398 dated Nov. 6, 2009.
Olthuis et al., "pH Sensor Properties of Electrochemically Grown Iridium Oxide," Sensors and Actuators, 1990, vol. B, No. 2, pp. 247-256.
Olthuis et al., "Preparation of Iridium Oxide and its Application in Sensor-Actuator Systems," Sensors and Actuators, 1991, vol. B, No. 4, pp. 151-156.
Parker et al., "The Intravenous Route to Blood Glucose Control," IEEE Engineering in Medicine and Biology, Jan./Feb. 2001, pp. 65-73.
Poitout et al., "A Glucose Monitoring System for on Line Estimation in Man of Blood Glucose Concentration Using a Miniaturized Glucose Sensor Implanted in the Subcutaneous Tissue and a Wearable Control Unit," Diabetologia, 1993 vol. 36, pp. 658-663.
Poitout et al., "Calibration in Dogs of a Subcutaneous Miniaturized Glucose Sensor Using a Glucose Meter for Blood Glucose Determination," Biosensors & Bioelectronics, 1992, vol. 7, pp. 587-592.
Reach, "A Method for Evaluating in vivo the Functional Characteristics of Glucose Sensors," Biosensors, 1986, vol. 2, pp. 211-220.
Schmidtke et al., "Accuracy of the One-Point in Vivo Calibration of "Wired" Glucose Oxidase Electrodes Implanted in Jugular Veins of Rats in Periods of Rapid Rise and Decline of the Glucose Concentration," Anal. Chem., 1998, vol. 70, pp. 2149-2155.
Shaw et al., "In vitro Testing of a Simply Constructed, Highly Stable Glucose Sensor Suitable for Implantation in Diabetic Patients," Biosensors & Bioelectronics, 1991, vol. 6, pp. 401-406.
Shichiri et al., "A Needle-Type Glucose Sensor—a Valuable Tool Not Only for a Self-Blood Glucose Monitoring But for a Wearable Artificial Pancreas-," Life Support Systems: the Journal of the European Society for Artificial Organs, Sep. 1984, vol. 2, supplement 1, pp. 7-9.
Shichiri et al., "An Artificial Endocrine Pancreas—Problems Awaiting Solution for Long-Term Clinical Applications of a Glucose Sensor," Frontiers Med. Biol. Engng., 1991, vol. 3, No. 4, pp. 283-292.
Shichiri et al., "Closed-Loop Glycemic Control with a Wearable Artificial Endocrine Pancreas Variations in Daily Insulin Requirements to Glycemic Response," Diabetes, Dec. 1984, vol. 33, pp. 1200-1202.
Shichiri et al., "Glycaemic Control in Pancreatectomized Dogs with a Wearable Artificial Endocrine Pancreas," Diabetologia, 1983, vol. 24, pp. 179-184.

Shichiri et al., "In Vivo Characteristics of Needle-Type Glucose Sensor—Measurements of Subcutaneous Glucose Concentrations in Human Volunteers-," Hormone and Metabolic Research, 1988, vol. 20, pp. 17-20.
Shichiri et al., "Membrane Design for Extending the Long-life of an Implantable Glucose Sensor," Diab. Nutr. Metab., 1989, vol. 2, pp. 309-313.
Shichiri et al., "Normalization of the Paradoxic Secretion of Glucagon in Diabetics Who Were Controlled by the Artificial Beta Cell," Diabetes, Apr. 1979, vol. 28, pp. 272-275.
Shichiri et al., "Telemetry Glucose Monitoring Device with Needle-Type Glucose Sensor: a Useful Tool for Blood Glucose Monitoring in Diabetic Individuals," Diabetes Care, May-Jun. 1986, vol. 9, No. 3, pp. 298-301.
Shichiri et al., "The Wearable Artificial Endocrine Pancreas with a Needle-Type Glucose Sensor: Perfect Glycemic Control in Ambulatory Diabetics," Acta Paediatr Jpn, 1984, vol. 26, pp. 359-370.
Shichiri et al., "Wearable Artificial Endocrine Pancreas with Needle-Type Glucose Sensor," The Lancet, Nov. 1982, pp. 1129-1131.
Shinkai et al., "Molecular Recognition of Mono- and Di-saccharides by Phenylboronic Acids in Solvent Extraction and as a Monolayer," J. Chem. Soc., 1991, pp. 1039-1041.
Shults et al., "A Telemetry-Instrumentation System for Monitoring Multiple Subcutaneously Implanted Glucose Sensors," IEEE Transactions on Biomedical Engineering, Oct. 1994, vol. 41, No. 10, pp. 937-942.
Sternberg et al., "Study and Development of Multilayer Needle-Type Enzyme-Based Glucose Microsensors," Biosensors, 1988, vol. 4, pp. 27-40.
Supplementary European Search Report for Appln. No. EP 02766221.2 dated Dec. 18, 2008.
Tamiya et al., "Micro Glucose Sensors Using Electron Mediators Immobilized on a Polypyrrole-Modified Electrode," Sensors and Actuators, 1989, vol. 18, pp. 297-307.
Tsukagoshi et al., "Specific Complexation with Mono- and Disaccharides That Can Be Detected by Circular Dichroism," J. Org. Chem., 1991, vol. 56, pp. 4089-4091.
Urban et al., "Miniaturized Multi-Enzyme Biosensors Integrated with pH Sensors on Flexible Polymer Carriers for In Vivo Applications," Biosensors & Bioelectronics, 1992, vol. 7, pp. 733-739.
Urban et al., "Miniaturized Thin-Film Biosensors Using Covalently Immobilized Glucose Oxidase," 1991, vol. 6, pp. 555-562.
Velho et al., "In Vivo Calibration of a Subcutaneous Glucose Sensor for Determination of Subcutaneous Glucose Kinetics," Diab. Nutr. Metab., 1988, vol. 3, pp. 227-233.
Velho et al., "Strategies for Calibrating a Subcutaneous Glucose Sensor," Biomed. Biochim. Acta, 1989, vol. 48 (11/12), pp. 957-964.
Von Woedtke et al.. "In Situ Calibration of Implanted Electrochemical Glucose Sensors," Biomed. Biochim. Acta, 1989, vol. 48 (11/12), pp. 943-952.
Wang et al., "Needle-Type Dual Microsensor for the Simultaneous Monitoring of Glucose and Insulin," Anal. Chem., Feb. 2001, vol. 73, No. 4, pp. 844-847.
Yamasaki et al., "Direct Measurement of Whole Blood Glucose by a Needle-Type Sensor," Clinica Chimica Acta, 1989, vol. 93, pp. 93-98.
Yokoyama, "Integrated Biosensor for Glucose and Galactose," Analytica Chimica Acta, 1989, vol. 218, pp. 137-142.

* cited by examiner

SAFETY LIMITS FOR CLOSED-LOOP INFUSION PUMP CONTROL

RELATED APPLICATIONS

This application is a Divisional of U.S. application Ser. No. 12/490,006, filed Jun. 23, 2009, incorporated herein by reference in its entirety, which is a Divisional of U.S. application Ser. No. 10/979,980, filed Nov. 3, 2004, incorporated herein by reference in its entirety, which is a Divisional of U.S. application Ser. No. 10/033,530, filed Dec. 26, 2001, incorporated herein by reference in its entirety, which claims priority from Provisional Application U.S. Application 60/318, 062, filed Sep. 7, 2001, incorporated herein by reference in its entirety and which claims priority from Provisional Application U.S. Application 60/335,664, filed Oct. 23, 2001, incorporated herein by reference in its entirety.

BACKGROUND OF THE INVENTION

1. Field of the Invention

The present invention relates generally to infusion pump systems for the delivery of infusion formulations and, in particular, to an implantable infusion pump system and process for delivering insulin to a user based in part on user-initiated signals which correspond to events which may affect the glucose level of the user.

2. Description of Related Art

In the medical arts, implantable infusion pumps are used for the programmed delivery of measured doses of an infusion formulation. (An infusion formulation is defined in the present disclosure as the substance being delivered by the infusion pump. This substance may comprise either a mixture of different components or it may be a single, pure substance.) A typical example of such use is the intraperitoneal delivery of an insulin formulation. FIG. 1 illustrates an example of this use. As shown in FIG. 1, an implantable infusion pump (IIP) 10 may be implanted in a patient below the skin and above the muscle in the abdomen. The IIP 10 will then dispense an infusion formulation (such as an insulin formulation) through the peritoneum wall 12 via a catheter 14. A lead 16 may connect IIP 10 to a sensing device (not shown) that is used to regulate the delivery of the infusion formulation.

In the case where the infusion formulation is an insulin formulation, the sensing device may regulate the delivery of the insulin formulation by sensing the levels of glucose in the patient. The delivery of the insulin formulation may then be performed in two ways. Information about the sensed glucose level may be provided to the patient (or to the patient's physician) through a communication device associated with the pump. The patient (or physician) would then manually administer an appropriate amount of the insulin formulation in accordance with the sensed glucose level. Alternatively, the sensed glucose level may be provided to a control device associated with the pump (such as a processor or other computing element) for controlling activation of the pump to deliver an appropriate amount of the insulin formulation in accordance with the sensed glucose level.

As discussed above, a typical use for an implantable infusion pump is the intraperitoneal delivery of an insulin formulation. Insulin is a protein hormone normally formed within the human pancreas. Because it regulates carbohydrate (sugar) metabolism, insulin is required for normal metabolic function. More specifically, insulin helps the body process glucose. To avoid medical problems, glucose levels should be maintained within a specific range. A normal range for glucose in the human body may be between 85 and 120 mg/dl.

In a non-diabetic person, insulin is secreted by the pancreas in small amounts throughout the day (basal rate of insulin secretion). In addition, the amount of insulin secreted by the pancreas may be modified under certain circumstances. For example, the pancreas of a non-diabetic person normally secretes larger amounts of insulin (bolus rate of insulin secretion) when the person ingests a meal to prevent postprandial hyperglycemia, i.e., abnormally increased sugar content in the blood.

In contrast to the non-diabetic person, a diabetic person's pancreas may not secrete the required amount of insulin. Thus, the diabetic person has to somehow artificially introduce the insulin into the body. One method of introducing the insulin is by the conventional insulin formulation injection method using a syringe. Using this method, the body's glucose level may be monitored (for example, by checking a blood sample) and the amount of insulin to be injected may be adjusted accordingly. For example, after a meal the glucose level may be monitored and an appropriate amount of insulin may be injected into the bloodstream of the individual.

In the alternative, a diabetic person may choose to use an infusion pump such as the implantable infusion pump described above and shown in FIG. 1. By using an infusion pump, a diabetic person may be able to adjust insulin delivery rates for the pump in accordance with the user's needs. These needs may be determined based on prior experience and/or the results of glucose monitoring (for example, by a sensing device in combination with a communication device). As an example, the basal and bolus delivery rates of an infusion pump may be adjusted in this manner.

In addition, infusion pumps may be engineered to function as an artificial pancreas. Such an infusion pump may deliver a specific amount of insulin formulation at specific intervals. As discussed above, a sensing device associated with the pump may monitor the glucose level of the user and the glucose level may then be used by the pump to automatically regulate the delivery of the insulin formulation. The automatic regulation may be carried out by a processor or other computing element associated with the pump.

The processor or other computing element may execute a closed-loop algorithm which may adjust insulin formulation delivery as a function of, for example, the rate of change over time of a sensed glucose level. These processes may be transparent to the user. Thus, the infusion pump in combination with a sensing device and closed-loop algorithm may be very beneficial to a diabetic person by automating the tasks of monitoring glucose levels and introducing an appropriate amount of insulin formulation based on the glucose level, with minimal input from the user (or the user's physician).

However, a problem exists with the method described above for the automated delivery of insulin using an infusion pump. The problem results from the fact that an individual's glucose level may be significantly affected by certain daily events. For example, when a person ingests food, glucose levels may rise due to ingested carbohydrates (sugars). In addition, it is believed that sleep affects glucose levels due to changes in the rate of glucose metabolism when a person sleeps. An individual's stress level may also affect glucose metabolism by increasing glucose levels in the bloodstream. Furthermore, the ingestion of medications may affect glucose levels within the body.

A properly functioning sensing device may detect a change in glucose level due to any of the events described above and provide the change in glucose level as an input to the closed-loop algorithm which may, in turn, provide an output to the pump to properly adjust the delivery of insulin formulation accordingly. However, in the case of an erroneous input to the closed-loop algorithm, for example, as a result of a malfunctioning sensing device, an erroneous glucose level may be indicated, leading to an erroneous adjustment in the amount of insulin delivered to the pump user. Under certain circumstances, such an error may result in extreme harm (including death) to the pump user.

Furthermore, it is believed that the body of a person merely anticipating the ingestion of a meal may have an increased level of insulin secretion. This increased insulin secretion may occur before any increase in glucose level can be detected by a sensing device. It is further believed that one reason for this leading insulin secretion reflex may be that the body is compensating, by early release of the insulin, for the time required for the insulin to react with the glucose. The secretion of insulin associated with meal anticipation is believed to lead any significant rise in glucose level by as much as 15-20 minutes. With present infusion pump systems for delivery of insulin formulation, such leading insulin secretion reflex may not be replicated, because the delivery of insulin by the pump may not occur until triggered by the detection of glucose by the sensing device.

Accordingly, there is a demand for an infusion pump system and process for delivery of insulin formulation which provides safety limits that may be used in conjunction with a closed-loop algorithm for adjusting insulin formulation delivery. The safety limits verify that levels of glucose detected by the infusion pump system's sensing device are consistent with events that may significantly affect the glucose level. In addition, there is a need for an infusion pump system and process for delivery of insulin formulation which may more accurately replicate the body's leading insulin secretion reflex.

SUMMARY OF THE DISCLOSURE

Therefore, it is an advantage of embodiments of the present invention to provide safety limits on the delivery of infusion formulation in response to a detected biological state, the safety limits being in the form of user-initiated signals corresponding to events that may significantly affect the biological state.

It is a further advantage of embodiments of the present invention to enable a user to initiate delivery of an insulin formulation before a change in a glucose level is detected in order to simulate a naturally occurring leading insulin secretion reflex.

It is a further advantage of embodiments of the present invention to provide diagnostic checks which compare an actual detected change in biological state with a change that is expected based on a user-initiated signal and alert a user to a possible malfunction when the results of the comparison are not within pre-determined limits.

It is a further advantage of embodiments of the present invention to alert a user if a detected biological state exists which should not exist in the absence of a user-initiated signal.

It is a further advantage of embodiments of the present invention to provide a user with a history of user-initiated signals, the history being accessible to the user and/or the user's physician.

These and other advantages are accomplished according to a system and process for communicating safety limits to a computing element in an infusion pump system. The safety limits may be communicated to the computing element in the form of user-initiated signals corresponding to information about events which may affect a biological state. The computing element may execute a closed-loop algorithm for adjusting the delivery of an infusion formulation base on a sensed biological state.

Preferred embodiments of the present invention provide a communication device for use with an infusion pump system for the peritoneal delivery of an insulin formulation to a diabetic user. In preferred embodiments, the communication device comprises a user interface having a plurality of user-selectable operators whereby a user may communicate information to the computing element about events that may affect a glucose level detected by a sensing device in the infusion pump system.

Depending upon the context of use, the invention may include various combinations of these features which function together to provide safety limits on the delivery of infusion formulation in response to a detected biological state. Various embodiments of the invention include one or more of these features. Preferred embodiments of the present invention contain each of these features.

These and other objects, features, and advantages of embodiments of the invention will be apparent to those skilled in the art from the following detailed description of embodiments of the invention, when read with the drawings and appended claims.

DETAILED DESCRIPTION OF EMBODIMENTS OF THE INVENTION

Figure 1:
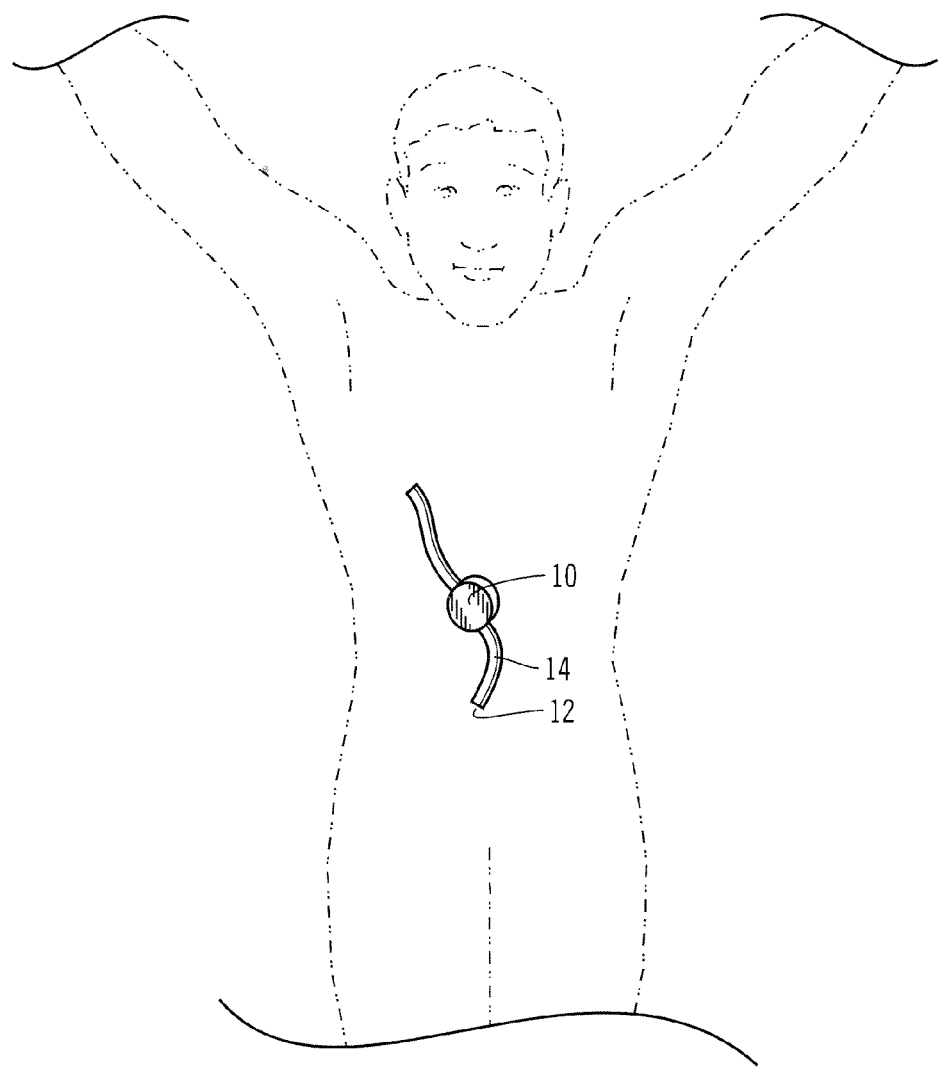
FIG. 1 shows a fragmented cutaway view of an exemplary environment of use for embodiments of the present invention in the peritoneal delivery of an insulin formulation.

In the following description of preferred embodiments, reference is made to the accompanying drawings which form a part hereof, and in which is shown by way of illustration specific embodiments in which the invention may be practiced. It is to be understood that other embodiments may be utilized and structural changes may be made without departing from the scope of preferred embodiments of the present invention, Environment of Use As discussed above, the present invention relates generally to infusion pump systems for the delivery of infusion formulations. The invention may be employed in various infusion environments including, but not limited to a biological implant environment. In preferred embodiments, the infusion pump system and process is configured for an implant environment within a human body, as shown in FIG. 1. However, other embodiments may be employed in other biological implant or non-implant environments.

Furthermore, in preferred embodiments, the infusion pump system and process is configured for delivery of an insulin formulation used to regulate glucose levels in a diabetic user. However, other embodiments may be employed in the delivery of other infusion formulations having other pharmacological properties.

As discussed above, FIG. 1 shows IIP 10 according to an embodiment of the invention. IIP 10 may be configured to be surgically implanted into a user, for example, at a particular location in the venous system, along the spinal column, in the peritoneal cavity, or other suitable site to deliver an infusion formulation to the user. However, further embodiments of the invention may be implemented as external infusion pumps, which connect to patients through suitable catheter devices or the like.

Infusion Pump System

The infusion pump system according to preferred embodiments of the invention employs a pump for delivering measured doses of an infusion formulation. In one embodiment, the pump comprises an electromagnetic mechanism that is activated to selectively drive infusion formulation to the user. The pump may be activated according to a programmed dispensing rate or schedule, or according to an actuation signal from a sensing device, timer, manual operator or other suitable means. In one preferred embodiment, the pump may be activated by a control signal communicated to the pump from a computing element which may be included in the infusion pump system.

The infusion pump system according to preferred embodiments of the invention further employs a sensing device for monitoring a selected biological state. In one embodiment, the selected biological state to be monitored may be the glucose level detected in the body of the pump user.

The infusion pump system according to preferred embodiments of the invention further employs a computing element which may, along with other pump control functions, execute a closed-loop algorithm which may continuously adjust infusion formulation delivery as a function of the sensed biological state. In one preferred embodiment, the closed-loop algorithm may continuously adjust insulin formulation delivery as a function of the rate of change of glucose levels over time. The computing element may comprise one or more programmable processors, logic circuits, or other hardware, firmware or software components configured for implementing the control functions described herein.

The infusion pump system according to preferred embodiments of the invention further employs a communication device for communicating user-initiated signals to the computing element. The user-initiated signals may be representative of events that affect the selected biological state. In one preferred embodiment, the communication device communicates with the computing element via a radio frequency ("RF") transceiver. However, in other embodiments other suitable means of data communication may be employed, such as, for example, ultrasonics.

Events Affecting Glucose Levels

As discussed above, certain events may significantly affect glucose production levels in the human body. Thus, these events may also significantly affect the amount of insulin produced in order to metabolize the glucose. For example, the ingestion of food may significantly increase the production of glucose in the body. This results in part from the fact that during digestion carbohydrates are broken down into glucose that then enters the bloodstream.

In addition, the amount and type of foods ingested affect the amount of glucose produced.

Similarly, exercise has been shown to lower glucose levels in the human body. Thus, exercise may result in a dip in glucose levels and a corresponding decrease in the amount of insulin formulation delivered by the body. Longer or more strenuous exercise events may result in a greater dip in glucose level than shorter and less strenuous exercise events.

Furthermore, sleep and stress may affect the body's ability to burn carbohydrates and therefore may affect glucose levels. For example, glucose metabolism has been found to be slower in a sleep deprived state. In addition, elevations of certain stress hormones within the body may also result in slower glucose metabolism. Thus, longer or shorter periods of sleep or stress may result in more or less significant changes in glucose levels.

An additional event that may affect insulin production is the ingestion of medication. Certain medications may affect an individual's sensitivity to insulin, i.e. a given amount of insulin may be more or less sufficient depending on whether a particular medication has been taken. The insulin sensitivity level of a user to a particular medication may be determined either by the user or by the user's physician, for example, by observing the user's glucose level after taking a particular medication.

Closed-Loop Algorithm Safety Limits

An infusion pump system for the automatic regulation of the delivery of insulin formulation should detect changes in glucose levels that may result from any of these events and adjust the amount of insulin formulation delivered accordingly. In an exemplary infusion pump system for the automatic regulation of the delivery of insulin formulation, a sensing device used in conjunction with the infusion pump may detect changes in the glucose level and provide this information as an input to a closed-loop algorithm. The typical closed-loop algorithm may then accordingly adjust the amount of insulin formulation delivered to the user.

However, dangers exists in the typical infusion pump system for the automatic regulation of the delivery of insulin formulation. One of the dangers is that the input to the closed-loop algorithm may be erroneous. In typical existing infusion pump systems for the automatic regulation of the delivery of insulin formulation, there may be no safety limits on the amount of insulin formulation that is delivered based on an erroneous input. In other words, the typical closed-loop algorithm may only examine the glucose level input and may have no way to verify whether the change in glucose level is a reasonable change, i.e., one that is consistent with an event affecting glucose levels.

Furthermore, as discussed above, the human body shows evidence of a leading insulin secretion reflex in response to anticipation of the ingestion of a meal. Typical existing infusion pump systems for the automatic regulation of the delivery of insulin formulation may not replicate this reflex, because the delivery of insulin formulation by the pump may not occur until triggered by the detection of glucose by the sensing device.

Therefore, according to preferred embodiments of the infusion pump system and process, the communication device comprises a user interface for entering user-initiated signals representative of events which may affect glucose levels in a biological system such as the human body. The user-initiated signals are provided to a computing element within the system which executes a closed-loop algorithm for adjusting insulin formulation delivery as a function of, for example, the rate of change over time of a sensed glucose level.

Figure 2:
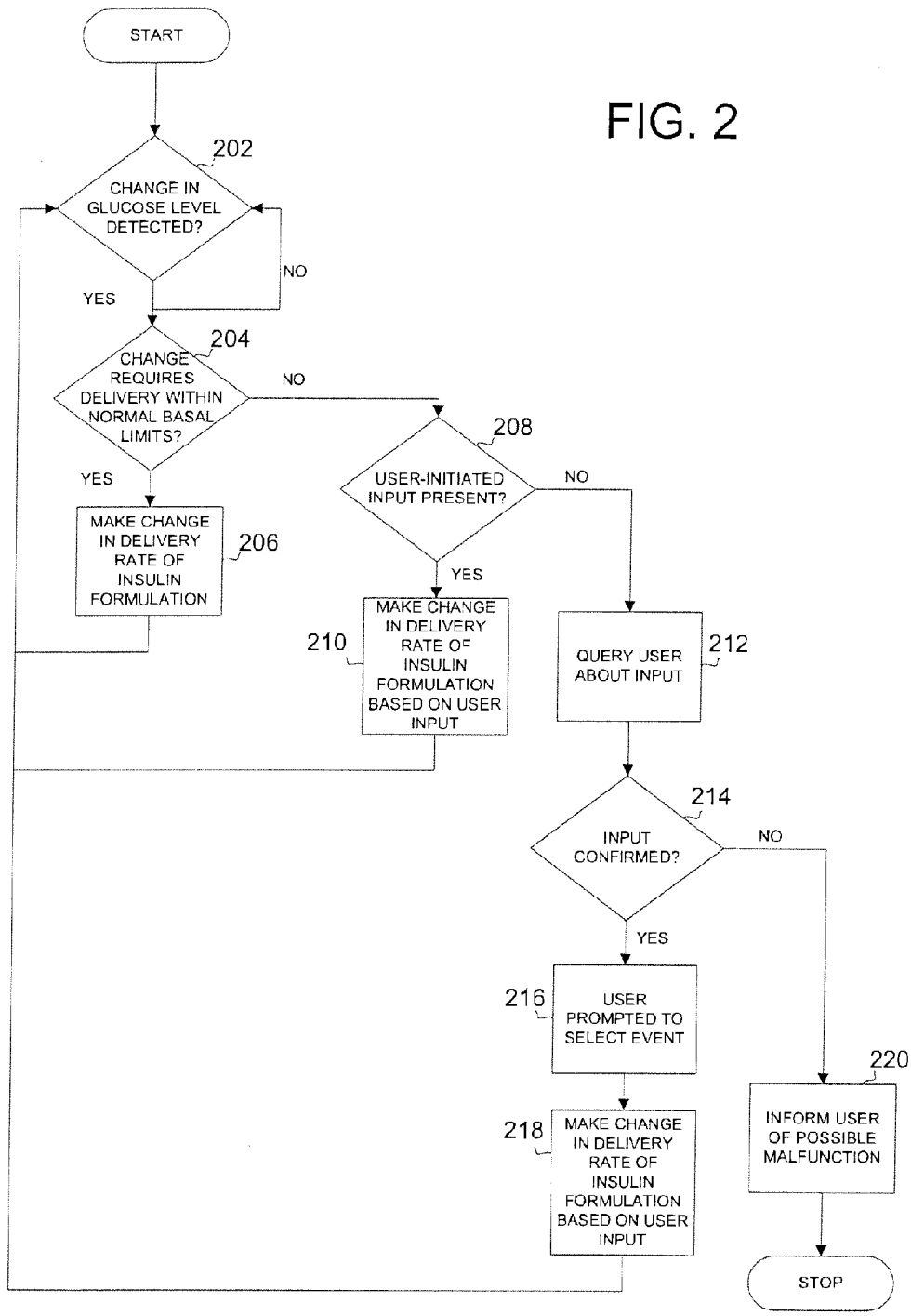
FIG. 2 shows a flowchart of a closed-loop algorithm for adjusting insulin formulation delivery as a function of the rate of change over time of a sensed glucose level and/or a user-initiated signal according to an embodiment of the invention.

FIG. 2 shows a flowchart of a closed-loop algorithm for adjusting insulin formulation delivery as a function of the rate of change over time of a sensed glucose level which incorporates one embodiment of the invention's system and process. As shown in step 202, the closed-loop algorithm may continuously check for changes in glucose level. A sensing device may detect the change in glucose level and may communicate the change to the computing element as a glucose level input to the algorithm. If no change is detected, the closed-loop algorithm may loop back to step 202, repeating this process until a change is detected. When a change occurs, the closed-loop algorithm may determine whether the amount of insulin formulation required based on the change in glucose level is within normal basal limits for the user, as shown in step 204.

The normal basal limits for the user may have been pre-programmed into the algorithm by the user or the user's physician. The normal basal limits may include maximum and minimum values of insulin formulation that may be delivered at one time. For example, if the user is in a basal state (i.e., a state requiring a basal rate of insulin secretion), the closed-loop algorithm may limit the delivery of insulin formulation to a maximum of fifty percent higher than a pre-programmed nominal basal rate of delivery. Similarly, the closed-loop algorithm may not allow the delivery rate to drop below a minimum allowable rate, for example, 0.2 units per hour.

Furthermore, the user (or the user's physician) may pre-program a user's basal profile into the closed-loop algorithm. This basal profile may indicate to the closed-loop algorithm, for example, that the user has a lower need for insulin at night.

Referring again to FIG. 2, if the change in glucose level requires an amount of insulin formulation that is within the pre-programmed basal limits and profile, the closed-loop algorithm may make a suitable adjustment to the delivery rate, as shown in step 206. The closed-loop algorithm may then loop back to step 202, repeating steps 204 through 206 described above.

However, if the detected change in glucose level requires the delivery of an amount of insulin formulation not within the basal limits or profile of the user, the closed-loop algorithm may scan "event inputs" to the closed-loop algorithm in order to determine if a user-initiated signal is present, as shown in step 208. If a user-initiated signal is present, the closed-loop algorithm may then process the signal to determine the adjustment in the insulin formulation delivery rate that corresponds to the user-initiated signal that is present at the event input, as shown in step 210.

On the other hand, in one embodiment, if no user-initiated signal is present at the event input to the closed-loop algorithm, the user may be queried, for example, via the communication device user interface, whether an event has occurred which requires the user to communicate a signal to the computing element, as shown in step 212. The communication device user interface may include user-selectable responses to the query.

If the user confirms that an event has occurred, as shown in step 214, the user may then be prompted to select the event, as shown in step 216. Once the user-initiated signal corresponding to the selected event is received at an event input of the closed-loop algorithm. The closed-loop algorithm may then process the signal to determine the adjustment in the insulin formulation delivery rate that corresponds to the user-initiated signal that is present at the event input, as shown in step 218.

In one preferred embodiment, if the user does not confirm that an event requiring an insulin formulation delivery amount outside of the pre-programmed basal limits has occurred, the closed-loop algorithm may alert the user to a possible malfunction in the infusion pump system, as shown in step 220. The closed-loop algorithm may then cease automatic control of the infusion pump and return to a manual operation so that the user or the user's physician may control the delivery rate.

Furthermore, in one preferred embodiment, the closed-loop algorithm may be programmed to perform diagnostic checks to ensure that a user-initiated signal communicated to an event input of the closed-loop algorithm is consistent with the glucose level detected by the sensing device. For example, if the user enters a meal event and the sensing device does not detect a corresponding change in the glucose level within a pre-programmed time, the closed-loop algorithm may alert the user to a possible malfunction in the infusion pump system. The closed-loop algorithm may then cease automatic control of the infusion pump and return to a manual operation so that the user or the user's physician may control the delivery rate.

As shown by the flowchart in FIG. 2, embodiments of the invention's system and process advantageously incorporates safety limits into the closed-loop algorithm to ensure that insulin formulation delivery amounts outside of a pre-programmed normal basal delivery rate correspond to events which may significantly affect glucose level. These events may be communicated by the user to the closed-loop algorithm event inputs via a communication device user interface. In one preferred embodiment, the events that may significantly affect glucose levels may comprise, for example, a meal event, an exercise event, a sleep event, a stress event, and a medication event.

Communication Device User Interface

The events may be communicated by the user to the closed-loop algorithm event inputs via a communication device user interface. User-selectable operators may be provided on the communication device user interface which allow a user to initiate a signal representing an event.

Thus, for example, the user may be able to press or otherwise select a user-selectable operator representing a sleep event before the user sleeps. In preferred embodiments, the closed-loop algorithm accepts the user-initiated signal at an event input and verifies that the glucose level input provided by the sensing device is consistent with the presence of the user-initiated signal at the event input of the closed-loop algorithm, as described above in relation to FIG. 2.

In one preferred embodiment, a user-initiated signal may initiate changes in the delivery amount of the infusion formulation independently of the sensing device input. For example, in one embodiment, a user may select a "meal" user-selectable operator on the user interface when the user is about to consume a meal. The user-initiated signal corresponding to the meal event communicated to the computing element may then initiate an immediate bolus delivery of insulin formulation by the pump even though the sensing device has not yet detected any rise in the glucose level.

Thus, the naturally occurring leading insulin secretion reflex phenomenon may be advantageously replicated by preferred embodiments of the infusion pump system and process by programming the closed-loop algorithm to deliver a suitable amount of insulin formulation based on the signal initiated by the user selecting the "meal" user-selectable operator, without the sensing device detecting any rise in glucose level.

In other preferred embodiments, the user interface may comprise user-selectable operators for selecting an "event ranking," for example, a degree, quantity, or measure of the selected event. As an example, if the user has selected a meal event, the user may be able to supplement this event information by selecting the size of the meal, for example, "light," "moderate," or "heavy." In addition, in some preferred embodiments, the user may be able to further supplement the event information by entering dietary information about the meal. For example, the user may be able to enter the meal's carbohydrate content, fat content, or other dietary information about the meal to be consumed. This information may be used to more accurately determine the expected effect of the meal on the glucose level.

In yet other preferred embodiments, if the user initially inputs one size for a meal but later decides to eat more or less, the user may be able to update the meal information although delivery of the insulin formulation by the infusion pump is already in progress based on the initial input. This may be done, for example, by selecting and inputting the event ranking which corresponds to the new size of the meal. In this embodiment, the computing element may dynamically (i.e. while delivery is in progress) re-calculate the amount of insulin formulation delivered based on both inputs.

As an example of this embodiment, the user may first select a light meal and input a corresponding signal. Then, after delivery is in progress, the user may decide that a heavy meal is preferable. The user may then select and input the event ranking which corresponds to a heavy meal. The computing element may then dynamically adjust the amount of insulin formulation delivered based on both the light and heavy inputs.

Similarly, the user interface may comprise user-selectable operators for selecting an event ranking for an exercise event. As an example, if the user has selected an exercise event, the user may be able to supplement this event information by selecting the type of exercise, the duration of the exercise, and/or whether the exercise is "light," "moderate," or "heavy."

In addition, the user interface may comprise user-selectable operators for selecting an event ranking for a sleep event. As an example, if the user has selected a sleep event, the user may be able to supplement this event information by selecting the amount of time the user expects to sleep.

Alternatively, the user may select an event ranking such as, but not limited to, "short," "moderate," or "long," corresponding to a short, moderate, or long interval of sleep. As an additional example, the user may simply press a "sleep" user-selectable operator before the sleep event and a "wake" user-selectable operator when the user awakes. In addition, or in the alternative, some preferred embodiments may enable the user to enter a time when the user expects to wake and the computing element may automatically calculate the duration of the sleep event and adjust the amount of delivered insulin formulation accordingly.

The user interface may further comprise user-selectable operators for selecting an event ranking for a stress event. As an example, if the user has selected a stress event, the user may be able to supplement this event information by selecting the ranking of stress, for example, "light," "moderate," or "heavy."

Furthermore, the user interface may comprise user-selectable operators for selecting an event ranking for a medication event. As an example, if the user has selected a medication event, the user may be able to supplement this event information by selecting the type of medication and/or the amount of the medication.

Alternatively, the user interface may comprise user-selectable operators which enable the user to, for example, simply select a level of sensitivity to insulin that is associated with the ingestion of a particular medication. A particular user's insulin sensitivity level associated with the ingestion of a particular medication may have been previously determined either by the user or by the user's physician. For example, a particular user's insulin sensitivity level may have been previously determined by observing the user's glucose level after taking the medication. Thus, the medication event ranking may be, for example, "low," "moderate," or "high," corresponding respectively to a low, moderate, or high sensitivity to insulin after taking a particular medication.

In one embodiment, the user-initiated signals are communicated to the computing element where they may be provided as an input to the closed-loop algorithm. The closed-loop algorithm may then incorporate the user-initiated signals into the algorithm's calculation of insulin formulation output, as described in reference to FIG. 2.

Figure 3:
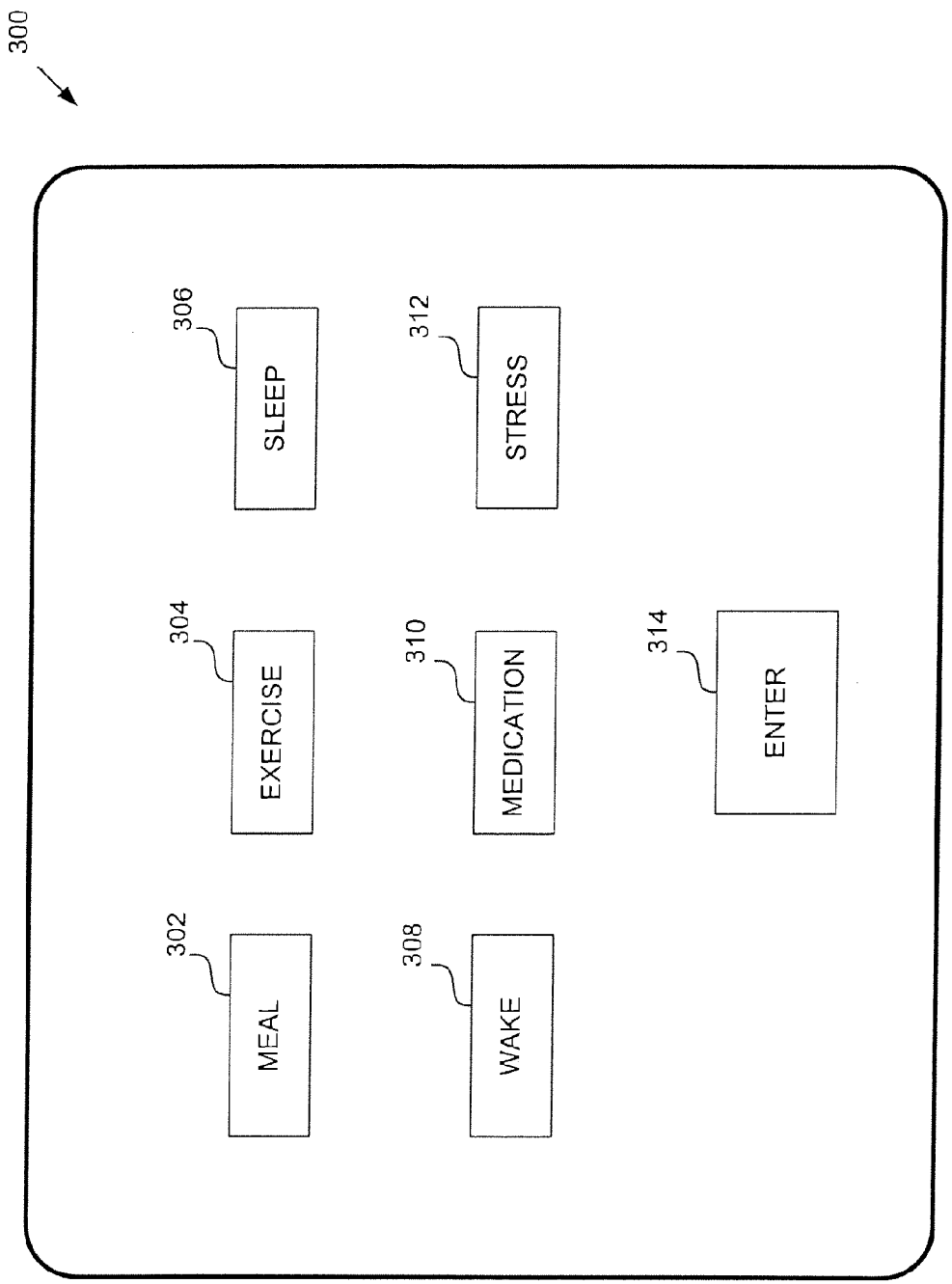
FIG. 3 shows an exemplary communication device user interface comprising a plurality of user-selectable operators corresponding to particular events, according to an embodiment of the invention.

FIG. 3 illustrates an example of a communication device user interface according to one preferred embodiment. In preferred embodiments, the communication device 300 is provided with a power source, for example, a battery, independent of the infusion pump power source. In other embodiments, the communication device 300 may be powered from the infusion pump power source.

Communication device 300 comprises an outer case or housing. This case or housing may be plastic, metal, or any other suitable material. Situated on the outer housing is the user interface. In the present preferred embodiment, the user interface comprises a plurality of user-selectable operators, each of the plurality of user-selectable operators corresponding to a particular event. Thus, communication device 300 comprises a simple user interface which enables a user to select an event simply by pressing or otherwise selecting the corresponding user-selectable operator.

In one preferred embodiment, the user may confirm the selection of an event by selecting an "enter" user-selectable operator 314. The inclusion of the "enter" user-selectable operator 314 may provide a measure of safety against accidental selection of an event user-selectable operator by, for example, bumping the communication device against another object. Thus, both the user-selectable operator corresponding to the desired event and the "enter" user-selectable operator 314 must be depressed in succession in order for a signal to be communicated to the computing element. In another embodiment, a confirmation screen may be used for a particularly important event, such as, for example, delivering a bolus. For example, upon the entering of a large meal event, the screen may respond by displaying "Large Meal Entered. Confirm?" Then, the user may depress enter again to confirm the event. This operation provides an extra level of safety.

In other embodiments, the "enter" user-selectable operator may be absent and other safety measures used against accidental selection. For example, in one embodiment, the user-selectable operators may be situated in a recessed portion of the communication device housing in order to avoid accidental selection. The user may be provided with a selection device, for example, a wand or pointer device, in order to access the user-selectable operators. In yet other embodiments, both safety measures may be employed.

In the embodiment of the communication device user interface shown in FIG. 3, a user may select the "meal" user-selectable operator 302 and then select the "enter" user-selectable operator 314 in order to communicate a signal to the computing element that the user is about to ingest a meal or is currently ingesting a meal. The closed-loop algorithm may then receive the user-initiated signal as an event input. In preferred embodiments, the computing element may confirm that the user-initiated signal was received, for example, by beeping, displaying a "signal received message," or other suitable method of informing the user that the computing element has received the signal.

Similarly, the user may select user-selectable operators 304, 306, 308, 310, or 312 in order to select the "exercise," "sleep," "wake," "medication," and "stress" events, respectively, and then select the "enter" user-selectable operator 314 in order to communicate the respective signal to the computing element that the user is about to exercise, is about to sleep, is now awake after sleeping, has taken medication, or is experiencing stress.

The embodiment of the communication device user interface shown in FIG. 3, advantageously provides the user with a user-friendly interface for communicating event information to the computing element. The amount of event information communicated to the computing element is kept to a minimum. However, embodiments of the infusion pump system and process may advantageously use even this minimal amount of event information to provide safety limits to insulin formulation delivery. For example, in one preferred embodiment using the communication device user interface shown in FIG. 3, the user's physician may be provided with password-protected access to the user's communication device in order to modify the closed-loop algorithm in accordance with parameters specific to the user.

As an example, a physician may determine the impact that taking a particular medication may have on the user's insulin sensitivity. The physician may then program the closed-loop algorithm in such a way that when the event input to the closed-loop algorithm receives a user-initiated signal corresponding to the "medication" user-selectable operator 310, the closed-loop algorithm may adjust the insulin formulation delivery in accordance with the physician's programmed instructions.

Similarly, the physician may modify the closed-loop algorithm to respond in a particular way to the selection by the user of user-selectable operators corresponding to other events. In addition, in some preferred embodiments, the computing element may maintain a history of user-initiated events that may be accessed by the user and/or the physician. For example, a history of the pump user's "meal" events may be maintained and accessed by the physician. The physician may advantageously use this information to advise the user on, for example, lifestyle patterns that may be affecting the user's health and well-being.

Figure 4:
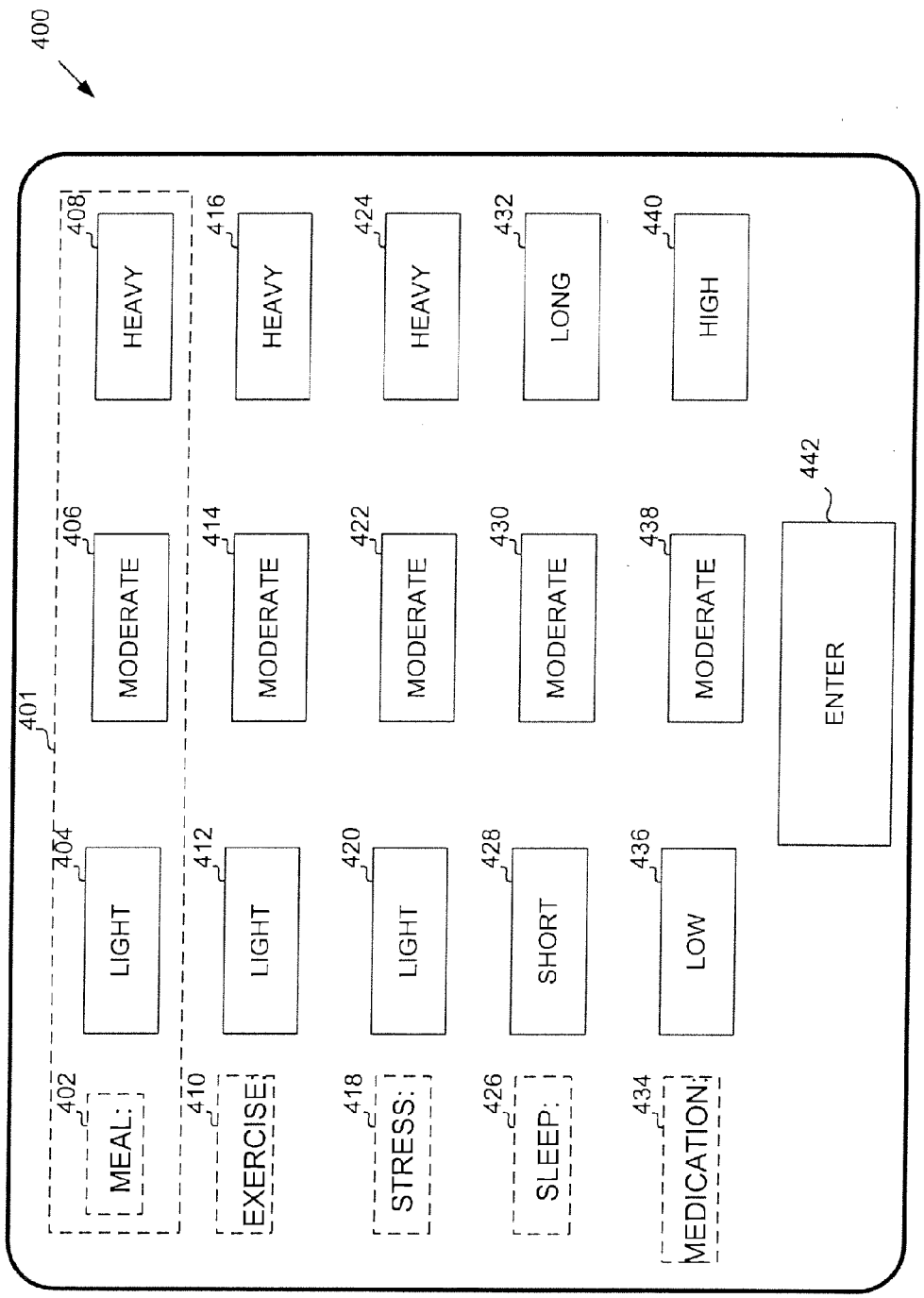
FIG. 4 shows an exemplary communication device user interface comprising a plurality, of user-selectable operators for selecting various event rankings corresponding to particular events, according to an embodiment of the invention.

FIG. 4 illustrates an example of a communication device user interface according to another preferred embodiment. Communication device 400 is provided with a power source, for example, a battery, independent of the infusion pump power source. In other embodiments, the communication device 400 may be powered from the infusion pump power source.

Communication device 400 comprises an outer case or housing. This case or housing may be plastic, metal, or any other suitable material. Situated on the outer housing is the user interface. In the present preferred embodiment, the user interface comprises a plurality of user-selectable operators for selecting various event rankings corresponding to particular events. The events may be indicated on the communication device 400 user interface by printed words, pictures, or other indicia representing the event. As an example, in FIG. 4, the events are indicated vertically along the left side of the communication device 400 user interface as "meal" 402, "exercise" 410, "stress" 418, "sleep" 426, and "medication" 434.

Event rankings associated with each event are situated to the right and in the same row as the associated event. In the embodiment shown in FIG. 4, the event indicators are not selectable but merely indicate the event associated with the user-selectable operators located in that particular row. For example, "meal" 402 event indicator is not selectable, but merely indicates that event rankings "light" 404, "moderate" 406, and "heavy" 410, located in the row indicated by reference numeral 401, are event rankings associated with the "meal" 402 event.

Similarly, event rankings "light" 412, "moderate" 414, and "heavy" 416 are event rankings associated with the "exercise" 410 event; event rankings "light" 420, "moderate" 422, and "heavy" 424 are event rankings associated With the "stress" 418 event; event rankings "short" 428, "moderate" 430, and "long" 432 are event rankings associated with the "sleep" 426 event; and event rankings "low" 436, "moderate" 438, and "high" 440 are event rankings associated with the "medication" 434 event.

In addition to the event ranking user-selectable operators described above, the communication device 400 user interface also comprises an "enter" user-selectable operator 442 which operates in a manner similar to that of "enter" user-selectable operator 314 described above in relation to FIG. 3.

In the embodiment of the communication device 400 user interface shown in FIG. 4, the user is able to enter more detailed information about a particular event than was the case for the communication device 300 user interface, shown in FIG. 3. As an example, for a "meal" event the user may locate the row on the communication device 400 user interface that has the "meal" 402 indicator. To the right of the "meal" 402 indicator there are three event rankings associated with the "meal" event, "light" 404, "moderate" 406, and "heavy" 408. These event rankings correspond, generally, to a light meal, a moderate meal, and a heavy meal, respectively.

Although in the embodiment shown in FIG. 4 there are three event rankings associated with each event, other embodiments may have more or less than three event rankings associated with a particular event. Furthermore, although in the embodiment shown in FIG. 4 certain event rankings are associated with a particular event, other event rankings are also possible in other embodiments. For example, although in the embodiment shown in FIG. 4 the event rankings associated with a meal event are light, moderate, and heavy, in other embodiments the event ranking descriptions may comprise more accurate quantitative descriptions. For example, in one embodiment, the event rankings associated with the meal event could be "less than X grams of carbohydrates," and "more than X grams of carbohydrates." The effects for a particular user of selecting any one of these event ranking user-selectable operators may be pre-programmed into the closed-loop algorithm and may, in some embodiments, be modified by a user's physician as described above in relation to FIG. 3.

Figure 5:
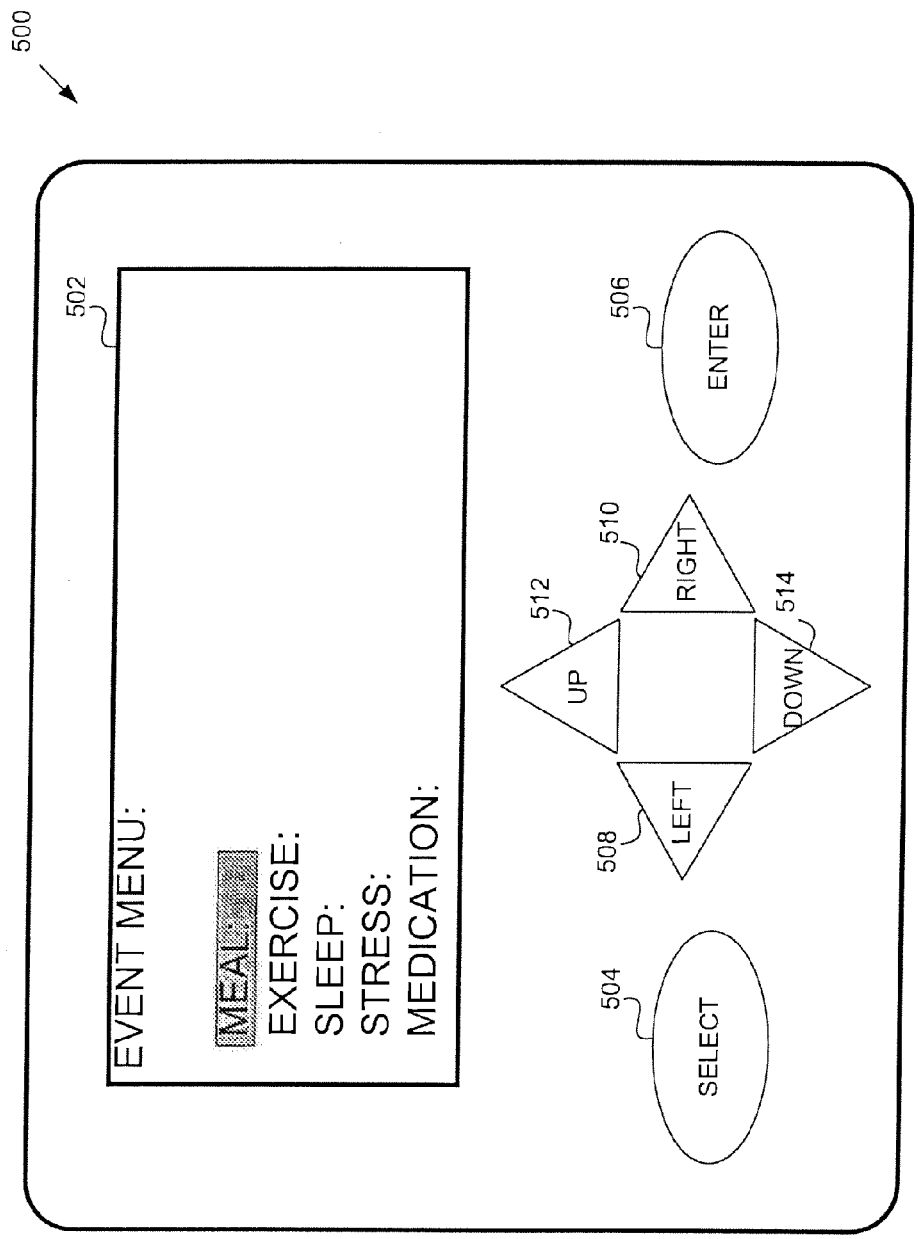
FIG. 5 shows an exemplary communication device user interface comprising a display for displaying events and event ranking information to a user, along with user-selectable operators for selecting and entering the events and event ranking information, according to an embodiment of the invention.

FIG. 5 illustrates an example of a communication device user interface according to another preferred embodiment. Communication device 500 is provided with a power source, for example, a battery, independent of the infusion pump power source. In other embodiments, the communication device 500 may be powered from the infusion pump power source.

Communication device 500 comprises an outer case or housing. This case or housing may be plastic, metal, or any other suitable material. Situated on the outer housing is the user interface. In the present preferred embodiment, communication device 500 user interface comprises display 502, "select" user-selectable operator 504, "enter" user-selectable operator 506, "cursor left" user-selectable operator 508, "cursor right" user-selectable operator 510, "cursor up" user-selectable operator 512, and "cursor down" user-selectable operator 514.

Display 502 may comprise any electronic display device for representing images and text. Display 502 may comprise, for example, a liquid crystal display ("LCD"), a thin film transistor ("TFT"), or any other type of suitable display device. Communication device 500 user interface may enable the user to display particular information on display 502 by selecting the "select" user-selectable operator 504 either alone or in combination with one or more other user-selectable operators.

For example, by initially selecting "select" user-selectable operator 504, a menu of events may be displayed to the user, as shown in FIG. 5. The user may then scroll through events on the menu by, for example, using the cursor user-selectable operators 508, 510, 512, and 514. The cursor highlights the currently selected event. In FIG. 5, the currently selected event is the "meal" event. In one preferred embodiment, once the desired event is highlighted, the user may then select the "enter" user-selectable operator 506 to proceed, for example, to an event ranking menu, as displayed in display 602, shown in FIG. 6.

Figure 6:
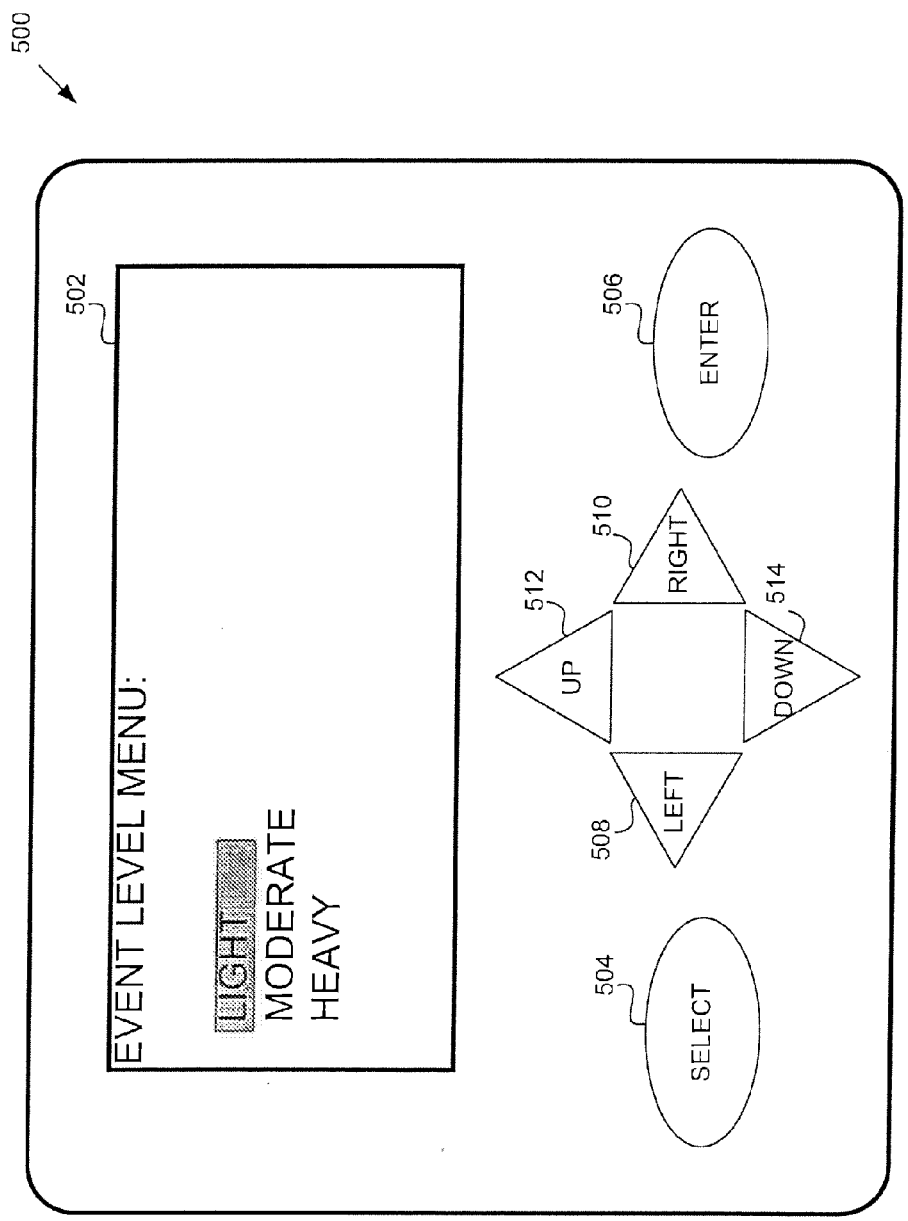
FIG. 6 shows an exemplary communication device user interface comprising an event ranking selection screen, according to an embodiment of the invention.

FIG. 6 shows an event ranking selection screen on display 502 of the communication device 500 user interface. Assuming that the user selected the meal event, the event rankings associated with the "meal" event are displayed on display 502. In one preferred embodiment, these event rankings are "light," "moderate," and "heavy." The user may then scroll through the displayed event rankings on the menu by, for example, using the cursor user-selectable operators 508, 510, 512, and 514. The cursor highlights the currently selected event ranking. In FIG. 6, the currently selected event ranking is the "light" event ranking. In one preferred embodiment, once the desired event ranking is highlighted, the user may then select, for example, the "enter" user-selectable operator 506 or the "select" user-selectable operator 504 to communicate a signal corresponding to the selected event ranking to the computing element.

Figure 7:
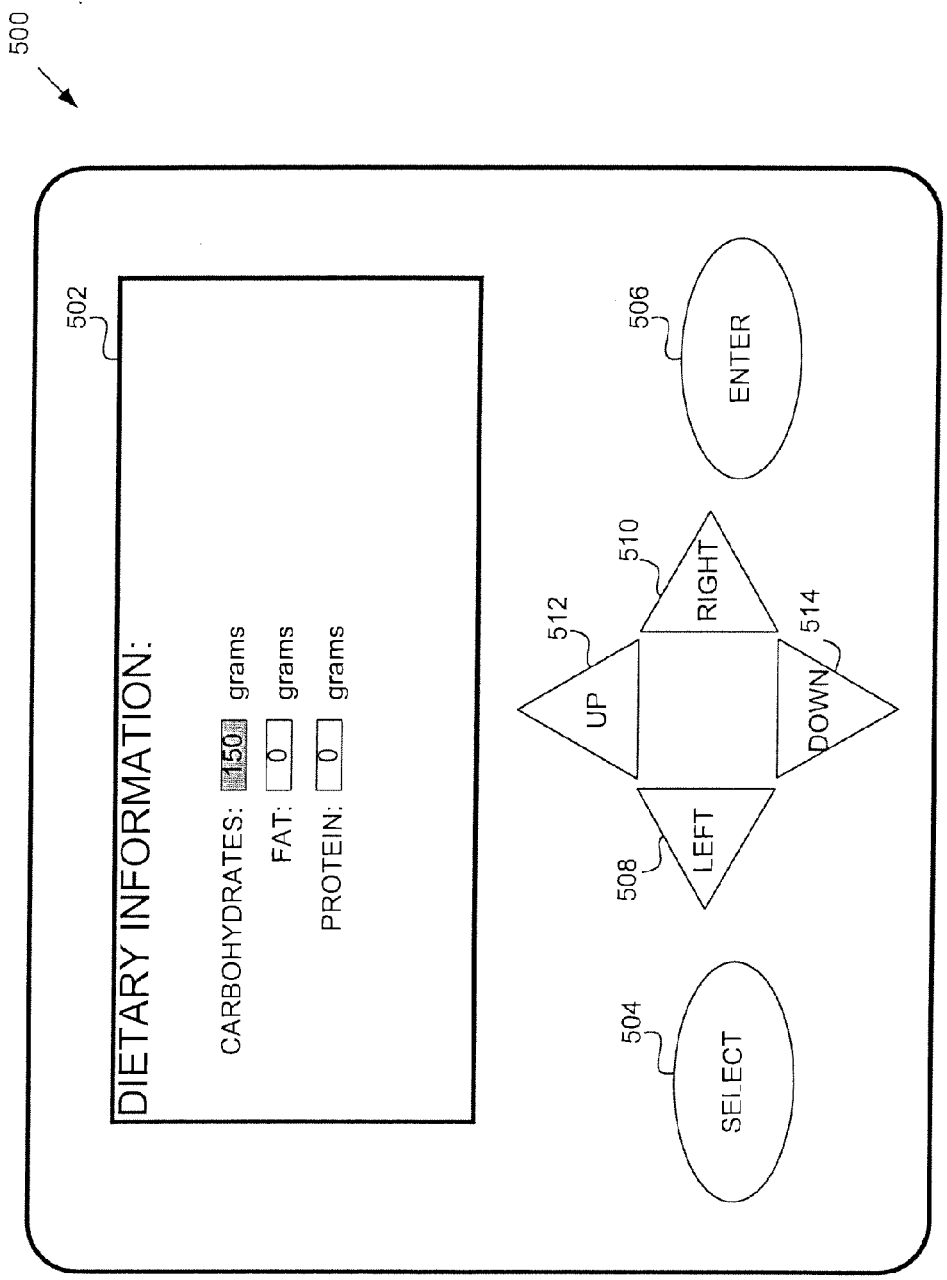
FIG. 7 shows an exemplary communication device user interface comprising a display for entering detailed dietary information about a meal event, according to an embodiment of the invention.

FIG. 7 shows another embodiment of the communication device 500 user interface wherein more detailed information may be entered regarding the meal event. In the embodiment of the communication device 500 user interface shown in FIG. 7, particular dietary substances and/or compounds may be displayed to the user in display 502. The user may enter an amount for each substance and/or compound. The amount may be expressed in a suitable unit of measurement, for example in grams. As an example, the user may use the cursor user-selectable operators 508, 510, 512, and 514 to highlight a particular substance or compound. The user may then select, for example, the "select" user-selectable operator 504 to select the substance or compound currently highlighted.

The user may then use, for example, the "cursor up" user-selectable operator 512 and "cursor down" user-selectable operator 514 to either increase or decrease, respectively, the displayed units of measurement. When the user has entered the dietary information, the user may select the "enter" user-selectable operator 506 in order to communicate the dietary information to the computing element.

Figure 8:
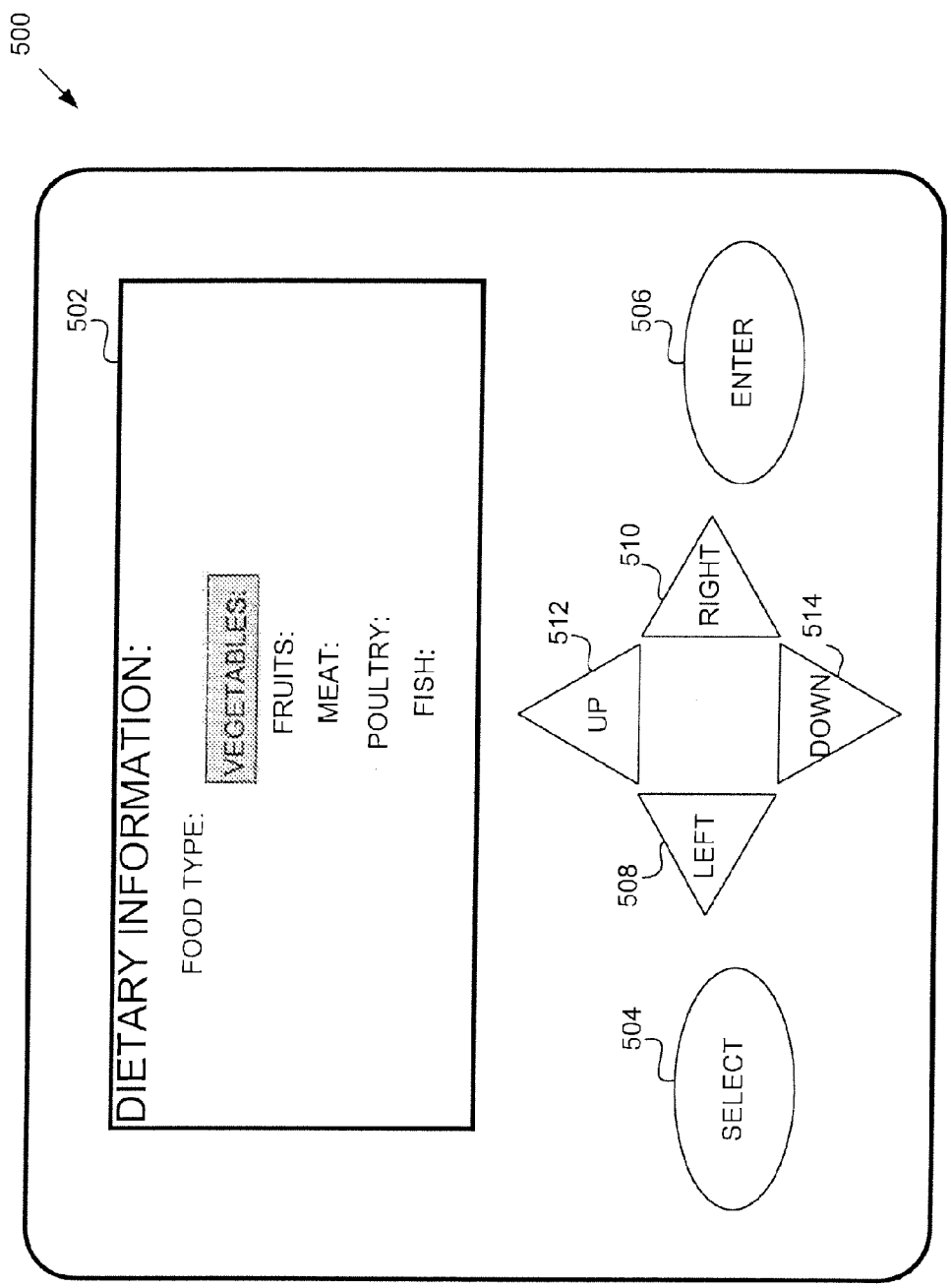
FIG. 8 shows an exemplary communication device user interface comprising a display for displaying a menu of selectable food types, according to an embodiment of the invention.

In yet other preferred embodiments, the user may select foods from food menus, as shown in FIG. 8. In one preferred embodiment, a menu of selectable food types may be displayed to the user in display 502 of the communication device 500 user interface after the meal event has been selected by the user. The user may then use the cursor user-selectable operators 508, 510, 512, and 514 to highlight a particular food type. In FIG. 8, the user has highlighted the "vegetable" food type. The user may then select, for example, the "select" user-selectable operator 504 or the "enter" user-selectable operator 506 in order to select the food type currently highlighted.

Figure 9:
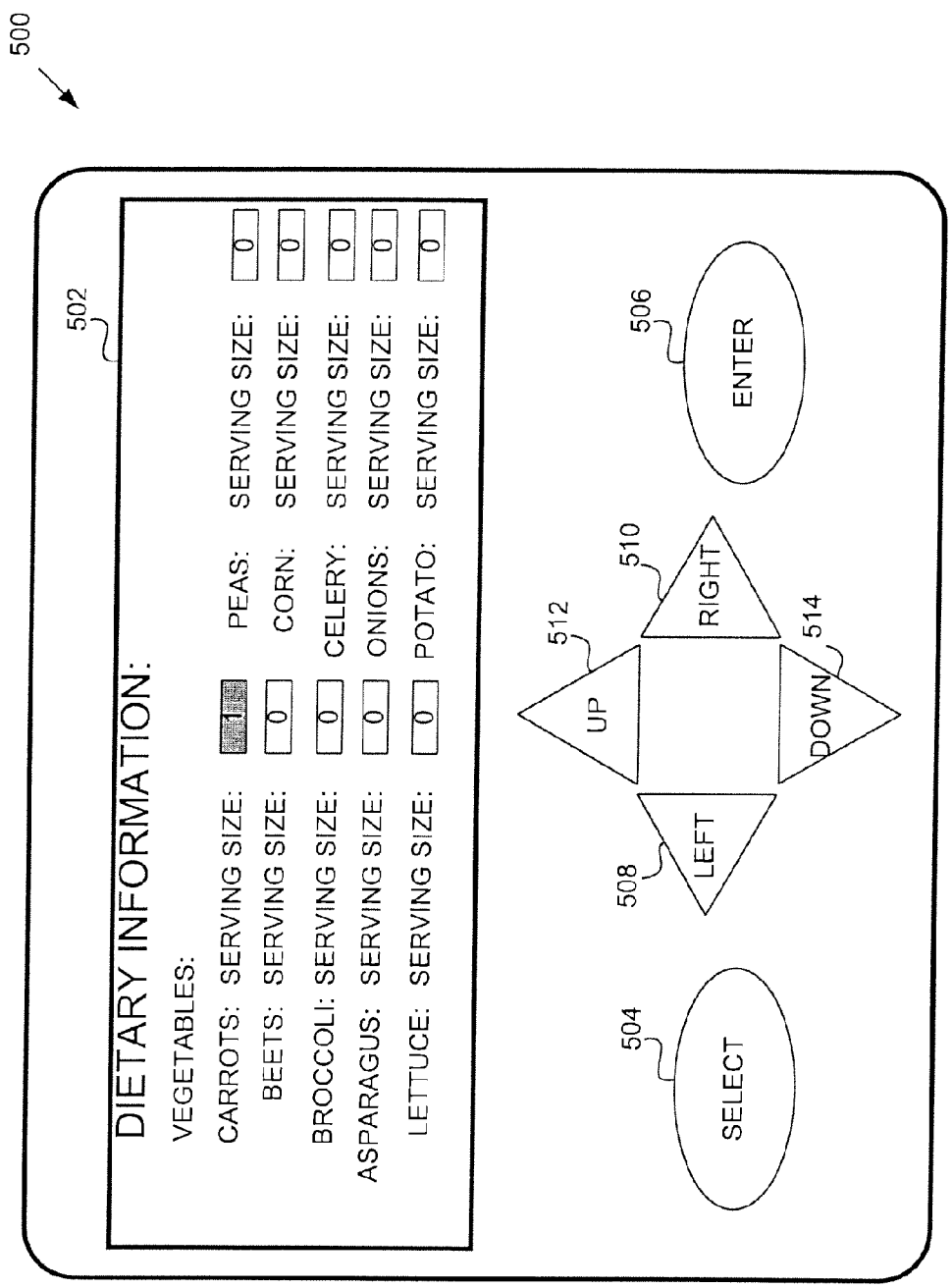
FIG. 9 shows an exemplary communication device user interface comprising a display for displaying a menu of foods corresponding to a selected food type, according to an embodiment of the invention.

In one preferred embodiment, when the currently highlighted food type is selected, a menu of foods corresponding to that food type may be displayed to the user, as shown in FIG. 9. FIG. 9 shows a selectable menu of vegetables in display 502. The user may use the cursor user-selectable operators 508, 510, 512, and 514 to highlight a particular vegetable. In one embodiment, the user may then use, for example, the "cursor up" user-selectable operator 512 and "cursor down" user-selectable operator 514 to either increase or decrease, respectively, the displayed number of serving sizes. Once the number of serving sizes has been selected, the user may then select, for example, either the "enter" user-selectable operator 506 or the "select" user-selectable operator 504 in order to communicate the dietary information to the computing element.

In preferred embodiments of the communication device 500 user interface shown in FIGS. 8 and 9, information about a particular food, such as, but not limited to, grams of fat per serving, grams of carbohydrates per serving, and grams of protein per serving, may be stored in a storage device located, for example, either in the computing element or within the communication device 500 itself. Thus, when a user selects a particular food and serving size, the dietary information may be calculated automatically by the computing element using the previously stored information. The closed-loop algorithm may then advantageously use this dietary information to more accurately determine the amount of insulin formulation to deliver.

Therefore, embodiments of the invention's infusion pump system and process provide a communication device user interface for entering user-initiated signals for communication to a computing element within the system. The user-initiated signals may be provided as event inputs to a closed-loop algorithm executed by a computing element. When the system's sensing device detects changes in a biological state, the closed-loop algorithm may be programmed to verify that an event input is present before delivering an amount of infusion formulation outside of pre-programmed basal limits.

The amount of insulin formulation to be delivered based on a particular event may be determined by pre-programmed data concerning the user. This pre-programmed data may be entered, for example, by the user and/or the user's physician or other medical professional. Thus, the event inputs provide safety limits to the amount of infusion formulation delivered in response to changes in a particular biological state.

Accordingly, a number of aspects and features of preferred embodiments of the communication device user interface described above may provide individually, or may be combined to provide user-initiated signals to a computing element within an infusion pump system. However, the foregoing description of preferred embodiments of the invention has been presented for the purposes of illustration and description. It is not intended to be exhaustive or to limit the invention to the precise forms disclosed. Many modifications and variations are possible in light of the above teaching.

For example, the events described above in preferred embodiments of the invention's system and process are examples of events which may lead to changes in insulin production by the pancreas of a non-diabetic person, and for which a user-initiated signal may be provided to a closed-loop algorithm, However, the above-named events should not be considered to be a limitation on the events which may affect glucose levels in the human body, and thus on the events for which a user-initiated signal may be provided to the closed-loop algorithm by embodiments of the invention's system and process.

Having disclosed exemplary embodiments and the best mode, modifications and variations may be made to the disclosed embodiments while remaining within the scope of the invention as defined by the following claims.

What is claimed is:

1. An infusion pump system to deliver an infusion formulation to a user, comprising:
   a sensing device to monitor glucose levels in the user;
   a computing element to receive sensing device input and to adjust delivery of the infusion formulation as a function of the rate of change of the glucose levels in the user over time, wherein the infusion formulation delivered to the user is limited to maximum and minimum values; and
   a pump in communication with the computing element to deliver the infusion formulation to the user;
   wherein if the adjusted delivery of the infusion formulation is not within the maximum and minimum values, the computing element determines whether a user-initiated signal is present in order to proceed.

2. The infusion pump system of claim 1, wherein delivery of the infusion formulation is limited to a maximum of a percentage higher than a pre-programmed nominal basal rate of delivery.

3. The infusion pump system of claim 1, wherein delivery of the infusion formulation is limited to a maximum of a percentage lower than a pre-programmed nominal basal rate of delivery.

4. The infusion pump system of claim 1, wherein a delivery rate of the infusion formulation is limited from dropping below a minimum allowable rate.

5. The infusion pump system of claim 1, wherein a delivery rate of the infusion formulation is limited from rising above a maximum allowable rate.

6. The infusion pump system of claim 1, wherein the pump is an implanted pump.

7. The infusion pump system of claim 1, wherein the pump is an external pump.

8. The infusion pump system of claim 1, wherein the infusion formulation is insulin.

9. The infusion pump system of claim 1, wherein if the adjusted delivery of the infusion formulation is not within the maximum and minimum values and there is no user-initiated signal present, the computing element queries the user.

10. A method of delivering an infusion formulation to a user, comprising:
monitoring glucose levels in the user;
receiving input of the glucose levels monitored and adjusting delivery of the infusion formulation as a function of the rate of change of the glucose levels in the user over time, wherein the infusion formulation delivered to the user is limited to maximum and minimum values;
delivering the infusion formulation to the user; and
determining whether a user-initiated signal is present in order to proceed, if the adjusted delivery of the infusion formulation is not within the maximum and minimum values.

11. The method of claim 10, wherein delivery of the infusion formulation is limited to a maximum of a percentage higher than a pre-programmed nominal basal rate of delivery.

12. The method of claim 10, wherein delivery of the infusion formulation is limited to a maximum of a percentage lower than a pre-programmed nominal basal rate of delivery.

13. The method of claim 10, wherein a delivery rate of the infusion formulation is limited from dropping below a minimum allowable rate.

14. The method of claim 10, wherein a delivery rate of the infusion formulation is limited from rising above a maximum allowable rate.

15. The method of claim 10, wherein delivering the infusion formulation is by an implanted pump.

16. The method of claim 10, wherein delivering the infusion formulation is by an external pump.

17. The method of claim 10, wherein the infusion formulation is insulin.

18. The method of claim 10, further including:
querying the user if the adjusted delivery of the infusion formulation is not within the maximum and minimum values and there is no user-initiated signal present.

19. An infusion pump system to deliver an infusion formulation to a user, comprising:
a sensing device to monitor glucose levels in the user;
a computing element to receive sensing device input and to adjust delivery of the infusion formulation as a function of the rate of change of the glucose levels in the user over time, wherein the infusion formulation delivered to the user is limited to maximum and minimum values; and
a pump in communication with the computing element to deliver the infusion formulation to the user;
wherein if the adjusted delivery of the infusion formulation is not within the maximum and minimum values and there is no user-initiated signal present, the computing element queries the user.

20. The infusion pump system of claim 19, wherein delivery of the infusion formulation is limited to a maximum of a percentage higher than a pre-programmed nominal basal rate of delivery.

21. The infusion pump system of claim 19, wherein delivery of the infusion formulation is limited to a maximum of a percentage lower than a pre-programmed nominal basal rate of delivery.

22. The infusion pump system of claim 19, wherein a delivery rate of the infusion formulation is limited from dropping below a minimum allowable rate.

23. The infusion pump system of claim 19, wherein a delivery rate of the infusion formulation is limited from rising above a maximum allowable rate.

24. The infusion pump system of claim 19, wherein the pump is an implanted pump.

25. The infusion pump system of claim 19, wherein the pump is an external pump.

26. The infusion pump system of claim 19, wherein the infusion formulation is insulin.

27. A method of delivering an infusion formulation to a user, comprising:
monitoring glucose levels in the user;
receiving input of the glucose levels monitored and adjusting delivery of the infusion formulation as a function of the rate of change of the glucose levels in the user over time, wherein the infusion formulation delivered to the user is limited to maximum and minimum values;
delivering the infusion formulation to the user; and
querying the user if the adjusted delivery of the infusion formulation is not within the maximum and minimum values and there is no user-initiated signal present.

28. The method of claim 27, wherein delivery of the infusion formulation is limited to a maximum of a percentage higher than a pre-programmed nominal basal rate of delivery.

29. The method of claim 27, wherein delivery of the infusion formulation is limited to a maximum of a percentage lower than a pre-programmed nominal basal rate of delivery.

30. The method of claim 27, wherein a delivery rate of the infusion formulation is limited from dropping below a minimum allowable rate.

31. The method of claim 27, wherein a delivery rate of the infusion formulation is limited from rising above a maximum allowable rate.

32. The method of claim 27, wherein delivering the infusion formulation is by an implanted pump.

33. The method of claim 27, wherein delivering the infusion formulation is by an external pump.

34. The method of claim 27, wherein the infusion formulation is insulin.

* * * * *